(12) United States Patent
Reid et al.

(10) Patent No.: US 6,455,466 B1
(45) Date of Patent: Sep. 24, 2002

(54) COMPOSITIONS AND METHODS FOR PREVENTING LEAF YELLOWING IN PLANTS

(75) Inventors: Michael A. Reid, Davis, CA (US); Antonio Ferrante, Gioia Sannitica (IT); Donald A. Hunter, Nelson (NZ); Wesley P. Hackett, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/618,604

(22) Filed: Jul. 17, 2000

(51) Int. Cl.$^7$ .......................... A01N 3/02; A01N 47/36
(52) U.S. Cl. ........................... 504/115; 504/217
(58) Field of Search ....................... 504/117, 115, 504/217

(56) References Cited

U.S. PATENT DOCUMENTS

| | | | |
|---|---|---|---|
| 4,245,101 A | * 1/1981 | Schulz et al. | 548/127 |
| 4,294,605 A | 10/1981 | Arndt et al. | 71/73 |
| 4,402,726 A | 9/1983 | Rusch et al. | 71/90 |
| 5,477,000 A | * 12/1995 | Sexena et al. | 800/200 |
| 6,022,830 A | * 2/2000 | Marquez et al. | 504/168 |

OTHER PUBLICATIONS

Richmond, A. E., et al., *Science*, 125:650–651 (1957).
Dyer, T. A., et al., *Journal of Experimental Botany*, 22:552–560 (1971).
Gan, S., et al., *BioEssay*, 18:557–565 (1996).
Tjosvold, Steven A., et al., *Hortscience*, 29:293–294 (1994).
Han, S. S., *Journal of the American Society for Horticultural Science*, 122::869–872 (1997).
Funnell, K. A., et al., *Hortscience*, 33:1036–103 (1998).
Genkov, T., Bulgarian Journal of Plant Physiology, 21:73–83 (1995).
Murthy, In vitro Cellular and Developmental Biology Plant 34::267–275 (1998).

* cited by examiner

*Primary Examiner*—Alton Pryor
(74) *Attorney, Agent, or Firm*—Townsend & Townsend Crew LLP

(57) ABSTRACT

This invention relates to compositions and methods for preserving plants and plant parts. In particular, it relates to compositions comprising compounds of Formula I to inhibit senescence in plants

21 Claims, 1 Drawing Sheet

COMPOSITIONS AND METHODS FOR PREVENTING LEAF YELLOWING IN PLANTS

FIELD OF THE INVENTION

This invention relates to compositions and methods for preserving plants and plant parts. In particular, it relates to compositions comprising substituted urea compounds (e.g., thidiazuron) to inhibit senescence in plants.

BACKGROUND OF THE INVENTION

Leaf yellowing is a common symptom of the onset of leaf senescence in plants, and is often a problem in horticulture or other agricultural production systems (Funnell, K. A., et al., *Hortscience*, 33:1036–103 (1998); Tollenaar, M., *Crop Science*, 31(1):119–124 (1991)). Yellow leaves are unsightly and reduce the quality, value and shelf life of ornamentals such as potted roses, potted and cut lilies, flowers of Alstroemeria, and leafy vegetables (Tjosvold, Steven A., et al., *Hortscience*, 29:293–294 (1994); Staby, G. L., et al., *Florists Rev.*, 161:38 (1977); Hibma, J. T., *Verslag Centrum voor Agrobiologisch Onderzoek*, 91:26 (1988)). Early onset of leaf senescence can affect agricultural productivity in diverse ways, for example yield in grain and legume crops and success of propagation of leafy cuttings (Martin del Molino, I. M., et al., *Physiol. Plant*, 66(3):503–508 (1986); Caldiz, et al., *Plant Growth Regulation*, 10(3):197–204 (1991); Finnan, J. M., et al., *Agriculture Ecosystems & Environment*, 69:27–35 (1998)).

Application of the synthetic cytokinin, benzylaminopurine (BAP) to leaves is known to prevent leaf yellowing and senescence (Richmond, A. E., et al., *Science*, 125:650–651 (1957); Dyer, T. A., et al., *Journal of Experimental Botany*, 22:552–560 (1971); Gan, S., et al., *Bio Essay*, 18:557–565 (1996)) This material along with Gibberellic acid (GA, another plant hormone with anti-senescence activity) are now in commercial use to prevent leaf yellowing in cut chrysanthemum flowers and potted roses, among others (van Doorn and de Wit, 1992; Tjosvold, Steven A., et al., *Hortscience*, 29:293–294 (1994); Han, S. S., *Journal of the American Society for Horticultural Science*, 122::869–872 (1997); Funnell, K. A., et al., *Hortscience*, 33:1036–103 (1998)).

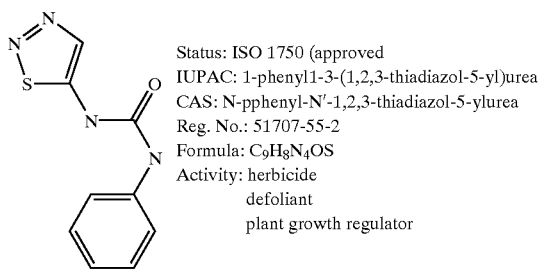

Status: ISO 1750 (approved)
IUPAC: 1-phenyl1-3-(1,2,3-thiadiazol-5-yl)urea
CAS: N-pphenyl-N'-1,2,3-thiadiazol-5-ylurea
Reg. No.: 51707-55-2
Formula: $C_9H_8N_4OS$
Activity: herbicide
  defoliant
  plant growth regulator The compound is registered for use as an herbicide and defoliant. It has high activity as a cytokinin, which probably is the basis of its herbicidal and defoliation properties. It is commonly used as substitute for BAP, zeatin, and other cytokinins that are used in plant tissue culture, because of its high activity (10 to 100 times that of BAP) and because plants do not metabolize it (Genkov, T., *Bulgarian Journal of Plant Physiology*, 21:73–83 (1995) and Murthy *In vitro Cellular and Developmental Biology Plant* 34::267–275 (1998)).

There is a real and continuing need for effective preservation formulations to inhibit senescence of leaves and other chlorophyll-containing plant organs. Such formulations can be used, for example, to preserve fresh cut flowers or potted plants. The present invention addresses these and other needs.

SUMMARY OF THE INVENTION

This invention provides compositions and methods for preserving plants, such as plant parts (e.g., cut flowers) and potted plants. The methods are based on the observation that compounds of Formula I are useful to prevent senescence in plants, particularly in chlorophyll-containing tissues. For example, the compounds maintain leaves in cut flowers or potted plants. In addition, in potted plants the compounds of the invention enhance growing buds and maintain flowers.

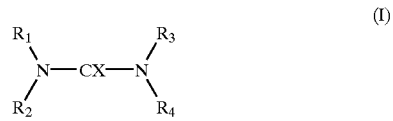

(I)

wherein:

$R_1$, and $R_4$ are independently selected from the group consisting of hydrogen and lower alkyl, $R_2$ and $R_3$ are independently selected from the group consisting of substituted or unsubstituted alkyl, substituted or unsubstituted cycloalkyl, substituted or unsubstituted aryl, and substituted or unsubstituted heteroaryl; and X is an oxygen or sulfur atom.

If $R_2$ or $R_3$ is alkyl it can be substituted or interrupted at least once by oxygen or sulfur. If $R_2$ or $R_3$ is cycloalkyl its can be substituted at least once by alkyl. If $R_2$ or $R_3$ is aryl substituted at least once by a member of the group consisting of alkyl, halogen, alkyl mercapto, alkoxy, trifluoromethyl and $NR_5R_6$, wherein $R_5$ and $R_6$ are independently selected from the group consisting of H or lower alkyl. In some embodiments $R_2$ and $R_1$ or $_3$ and $R_4$ together with the N atom, form a heterocyclic or heteroaryl ring, such as a morpholino, a piperidino, or a pyrrolidino moiety.

A preferred compound to use in the methods is 1-phenyl-3-(1,2,3-thiadiazol-5-yl)urea, referred to as thidiazuron. Other preferred compounds include N-(2-chloro-4-pyridyl)-N'-phenylurea and 1,3-diphneyl urea.

The compositions of the invention may contain other constituents such as plant nutrients and surfactants, depending upon the particular use. The methods are useful with all plants, particularly cut flowers and potted plants.

DEFINITIONS

The term "plant" includes whole plants, and plant parts including shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary). For example, the term refers to cut flowers or other organs. The class of plants that can be used in the method of the invention includes the class of higher and lower plants, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multi-valent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkoxy," refers to those groups having an alkyl group attached to the remainder of the molecule through an oxygen, atom.

The term "alkyl mercapto," refers to those groups having an alkyl group attached to the remainder of the molecule through a sulfur atom.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings), which are fused together or linked covalently. "Heteroaryl" are those aryl groups having at least one heteroatom ring member. Typically, the rings each contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 1,2,3, thiadiazol-5-yl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from, for example: —OR', =O, =NR', =N—OR', —NR'R", —SR', -halogen, —SiR'R"R'", —OC(O)R', —C(O)R', —$CO_2R'$, CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$–$C_4$) alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl, (unsubstituted aryl)-($C_1$–$C_4$) alkyl, (unsubstituted aryl)oxy-($C_1$–$C_4$)alkyl and perfluoro ($C_1$–$C_4$)alkyl.

Two of the substituents on adjacent atoms of the aryl ring may optionally be replaced with a substituent of the formula —T—C(O)—(CH$_2$)$_q$—U—, wherein T and U are independently —NH—, —O—, —CH$_2$— or a single bond, and the subscript q is an integer of from 0 to 2. Alternatively, two of the substituents on adjacent atoms of the aryl ring may optionally be replaced with a substituent of the formula -A-(CH$_2$)r-B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —$(CH_2)_s$—X—$(CH_2)_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$)alkyl.

DETAILED DESCRIPTION

Figure 1:
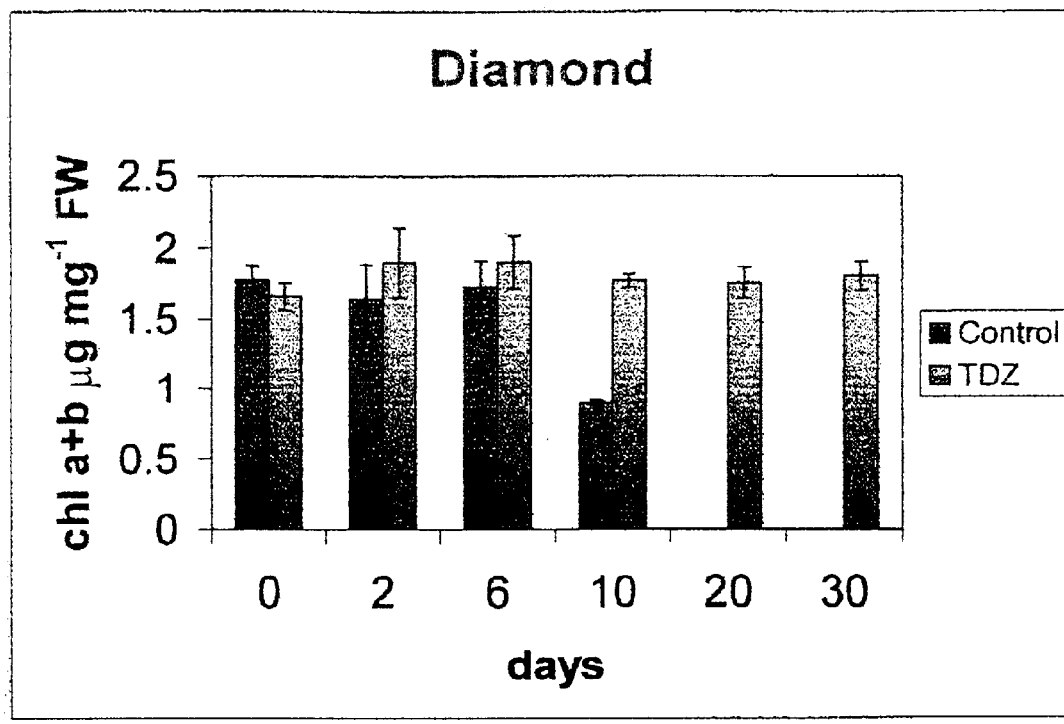
FIG. 1 shows chlorophyll content of leaves of control flowers and flowers treated with compositions of the invention.

The present invention provides new compositions and methods for enhancing the viability of plants (e.g., fresh cut flowers and potted plants). The compositions are typically an aqueous solution (e.g., a plant nutrient solution) which contains a compound of Formula I. A preferred compound is thidiazuron, the common name for N-phenyl-N'-1,2,3-thiadiazol-5-ylurea. The preparation of these compounds and their use as defoliants is described, for example, in U.S. Pat. Nos. 4,245,101, 4,294,605, 4,402,726. Such compounds are also commercially available from Aventis, Sigma, or Nor-Am.

The amount of compound of Formula I in the compositions of the invention can vary widely, but is typically from about 100 nM to about 100 mM, preferably from about 1 $\mu$M to about 100 gM. The compounds may be used alone or in combination with known additives as described below.

In some embodiments (e.g., when applied to potted plants), the compositions of the invention may be a plant nutrient composition and will thus comprise some or all of the chemical elements commonly recognized as being essential for plant growth. These include the essential macronutrients (e.g., potassium, calcium, magnesium, phosphorous, nitrogen, and sulfur) and the essential micronutrients (e.g., iron, copper, nickel, manganese, zinc, molybdenum, boron, and chlorine). Other elements that are beneficial to plant growth include sodium, cobalt, and silicon. The preparation and use of plant nutrient compositions is well known in the art. One of skill can prepare plant nutrient compositions containing some or all of the above elements at the appropriate concentrations according to well known techniques. In the case of cut flowers and other plant parts, the nutrient composition may also comprise sugar, such as sucrose or dextrose.

The compositions of the invention may also comprise one or more surface-active agents such as wetting agents, dispersing agents, emulsifying agents, or suspending agents may be included. For example, any number of surfactants may be used. The surfactant can comprise a nonionic, anionic, cationic, or zwitterionic surfactant. The surfactant can be present in the composition of the invention as formulated or, alternatively, the surfactants can be introduced during application to the plant. In the case of cut flowers, the compositions may contain other additives such as citric, phosphoric or acetic acid or suitable salts thereof and biocides.

The composition may also be in the form of an aqueous gel of sufficient strength to support the plant part even in the absence of inert solid aggregates. In addition to clays and natural gums, several types of water-absorbing cross-linked polymers have been used to form aqueous gels that are useful as a plant growth medium or plant preservation medium.

The compositions can be applied to the plants according to well known techniques. In the case of cut flowers and other plants parts, the plant part can simply be placed in a composition of the invention. In the case of potted plants, the composition can be applied as a foliar spray or be applied to the soil.

The compositions and methods of the invention can be used with essentially any plant. Thus, the invention has use over a broad range of plants, including species from the genera Asparagus, Brassica, Citrus, Capsicum, Cucumis, Cucurbita, Daucus, Fragaria, Helianthus, Heterocallis, Hyoscyamus, Lactuca, Linum, Lolium, Lupinus, Lycopersicon, Malus, Majorana, Nicotiana, Olea, Oryza, Panieum, Pannesetum, Persea, Phaseolus, Pisum, Pyrus, Prunus, Raphanus, Ricinus, Senecio, Sinapis, Solanum, Theobromus, Trigonella, Vicia, Vitis, and Vigna.

In the case of cut flowers, the present invention can be used with virtually any flower that is commonly sold as fresh cut. Such plants include, for example, Alstroemeria, roses, tulips, carnations, and mums, chrysanthemums, euphorbia, gladiolus, baby's breath, daisies, orchids, lilies, iris, and snapdragons.

The following examples are offered to further illustrate, but not limit the process of this invention.

EXAMPLES

The following examples are offered to illustrate, but not to limit the claimed invention.

Example 1

The model system used in the experiments was cut stems of Alstroemeria an important cut flower whose flowers normally long outlast the relatively short-lived leaves.

In a preliminary experiment with cut flowers of Alstroemeria (cv. diamond), the flowers were placed in deionized water (DI) or a solution containing 1 $\mu$M TDZ. The chlorophyll content of the leaves was measured as described by Lichenhaler, *Methods in Enzymology* 14:350 (1987). The chlorophyll content of the leaves was of the TDZ-treated plants remained high throughout the experiment and by 10 days was significantly higher than the concentration in leaves of flowers held in DI. By 20 days, there was no detectable chlorophyll in the leaves of the control flowers (see, FIG. 1).

In subsequent experiments it was shown that TDZ is much more effective than BAP or GA3, and that a 24 hour pulse pre-treatment (a common pretreatment time for commercial producers of cut flowers) with 10 $\mu$M TDZ is as effective as continuous treatment with 1 $\mu$M TDZ.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting senescence in a plant part selected from the group consisting of a cut floral organ, and a cut vegetative organ, the method comprising contacting the plant part with a composition comprising a compound of the formula:

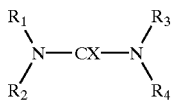

wherein:
- $R_1$, and $R_4$ are independently selected from the group consisting of hydrogen and lower alkyl,
- $R_2$ and $R_3$ are independently selected from the group consisting of substituted or unsubstituted alkyl, substituted or unsubstituted cycloalkyl, substituted or unsubstituted aryl, and substituted or unsubstituted heteroaryl; and
- and X is an oxygen or sulfur atom to inhibit senescence in the plant part.

2. A method of claim 1, wherein $R_2$ or $R_3$ is said substituted alkyl substituted or interrupted at least once by oxygen or sulfur.

3. The method of claim 1, wherein $R_2$ or $R_3$ is said substituted cycloalkyl substituted at least once by alkyl.

4. The method of claim 1, wherein $R_2$ or $R_3$ is said substitle aryl substituted at least once by a member of the group consisting of alkyl, halogen, all mercapto, alkoxy, trifuoromethyl and $NR_5R_6$, wherein $R_5$ and $R_6$ are independently selected from the group consisting of H and lower alkyl.

5. The method of claim 1, wherein either $R_1$ and $R_2$ or $R_3$ and $R_4$ together with the N atom, form a heterocyclic or heteroaryl ring.

6. The method of claim 5, wherein the heterocyclic ring is selected from the group consisting of a morpholino, a piperidino, and a pyrrolidino moiety.

7. The method of claim 1, wherein the compound is 1-phenyl-3-(1,2,3-thiadiazol-5-yl)urea.

8. The method of claim 1, wherein the plant part is a cut flower.

9. The method of claim 1, wherein the composition is a plant nutrient solution.

10. The method of claim 1, wherein the composition further comprises a surfactant.

11. A method of inhibiting senescence in a whole plant, the method comprising contacting the plant with a composition comprising a compound of the formula:

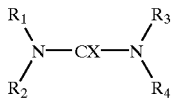

wherein:
- R1, and R4 are independently selected from the group consisting of hydrogen and lower alkyl,
- R2 and R3 are independently selected from the group consisting of substituted or unsubstituted alkyl, substituted or unsubstituted cycloalkyl, substituted or unsubstituted aryl, and substituted or unsubstituted heteroaryl
- and X is an oxygen or sulfur atom, wherein the compound is at a concentration from about 1 μM to about 100 μM to inhibit senescence in the whole plant.

12. The method of claim 11, wherein R2 or R3 is said substituted alkyl substituted or interrupted at least once by oxygen or sulfur.

13. The method of claim 11, wherein R2 or R3 is said substituted cycloalkyl substituted at least once by alkyl.

14. The method of claim 11, wherein R2 or R3 is said substituted aryl substituted at least once by a member of the group consisting of alkyl, halogen, alkyl mercapto, alkoxy, trifluoromethyl and NR5R6, wherein R5 and R6 are independently selected from the group consisting of H and lower alkyl.

15. The method of claim 11, wherein either R1 and R2 or R3 and R4 together with the N atom, form a heterocyclic or heteroaryl ring.

16. The method of claim 15, wherein the heterocyclic ring is selected from the group consisting of a morpholino, a piperidino, and a pyrrolidino moiety.

17. The method of claim 11, wherein the compound is 1-phenyl-3-(1,2,3-thiadiazol-5-yl)urea.

18. The method of claim 11, wherein the composition further comprises a surfactant.

19. The method of claim 11, wherein the step of contacting is carried out by foliar application of the composition.

20. A method of inhibiting senescence in a cut flower, the method comprising contacting the cut flower with a composition comprising a compound of the formula:

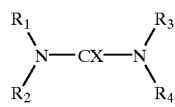

wherein:
- R1, and R4 are independently selected from the group consisting of hydrogen and lower alkyl,
- R2 and R3 are independently selected from the group consisting of substituted or unsubstituted alkyl, substituted or unsubstituted cycloalkyl, substituted or unsubstituted aryl, and substituted or unsubstituted heteroaryl; and
- and X is an oxygen or sulfur atom to ingibit senescence in the whole plant.

21. The method of claim 20, wherein the compound is 1-phenyl-3-(1,2,3-thiadiazol-5-yl)urea.

* * * * *